(12) United States Patent
Saito et al.

(10) Patent No.: US 8,668,923 B2
(45) Date of Patent: Mar. 11, 2014

(54) FILMY COMPOSITIONS

(75) Inventors: Yoshinobu Saito, Ibaraki (JP); Shinya Yamazaki, Ibaraki (JP); Uhei Tamura, Ibaraki (JP); Tetsuo Nishina, Ibaraki (JP)

(73) Assignee: P & PF Co., Ltd., Ibaraki-shi, Osaka (JP)

( * ) Notice: Subject to any disclaimer, the term of this patent is extended or adjusted under 35 U.S.C. 154(b) by 1481 days.

(21) Appl. No.: 11/885,454

(22) PCT Filed: Dec. 14, 2006

(86) PCT No.: PCT/JP2006/324914
§ 371 (c)(1),
(2), (4) Date: Aug. 31, 2007

(87) PCT Pub. No.: WO2007/072723
PCT Pub. Date: Jun. 28, 2007

(65) Prior Publication Data
US 2010/0166868 A1    Jul. 1, 2010

(30) Foreign Application Priority Data
Dec. 19, 2005  (JP) ................. 2005-365625

(51) Int. Cl.
*A61K 9/70* (2006.01)
*A61K 9/00* (2006.01)
*A61K 8/02* (2006.01)
*A61K 9/14* (2006.01)

(52) U.S. Cl.
USPC ............ 424/443; 424/400; 424/401; 424/489

(58) Field of Classification Search
USPC .................. 424/423, 400, 401, 489
See application file for complete search history.

(56) References Cited

U.S. PATENT DOCUMENTS

| | | | | |
|---|---|---|---|---|
| 2,577,218 A | * | 12/1951 | Van Der Waarden | ........... 516/29 |
| 5,021,405 A | * | 6/1991 | Klimisch | ......................... 514/63 |
| 5,951,989 A | * | 9/1999 | Heymann | ...................... 424/401 |
| 6,344,205 B1 | * | 2/2002 | Grimm et al. | ................. 424/401 |
| 7,717,996 B2 | * | 5/2010 | Bumm et al. | ............. 106/164.01 |
| 2003/0091617 A1 | * | 5/2003 | Mrozinski et al. | ............ 424/443 |
| 2004/0248486 A1 | * | 12/2004 | Hodson | ............................ 442/79 |
| 2006/0127458 A1 | * | 6/2006 | Kiser et al. | ..................... 424/443 |
| 2006/0155013 A1 | | 7/2006 | Bumm et al. | |

FOREIGN PATENT DOCUMENTS

| | | |
|---|---|---|
| CN | 1458949 | 11/2003 |
| FR | 2563104 A1 * | 4/1985 |
| GB | 1312083 | 4/1973 |
| JP | 53-091912 | 8/1978 |
| JP | 53-091913 | 8/1978 |
| JP | 62-081432 | 4/1987 |
| JP | 63-280798 | 11/1988 |
| JP | 02-022400 | 1/1990 |
| JP | 2003-147400 | 5/2003 |
| JP | 2003-160693 | 6/2003 |
| JP | 2003-518010 | 6/2003 |
| JP | 2003-213038 | 7/2003 |
| WO | 0222722 A1 | 3/2002 |
| WO | WO 2004033572 A1 * | 4/2004 |

OTHER PUBLICATIONS

Merriam Webster Online Dictionary, www.merriam-webster.com/dictionary/granule, downloaded on Sep. 29 2010.*
Supplementary European Search Report for EP 06834668 dated Mar. 18, 2008, three pages.
US 4,962,130, 10/1990, Yanagida et al. (withdrawn)*

* cited by examiner

*Primary Examiner* — Abigail Fisher
(74) *Attorney, Agent, or Firm* — Rankin, Hill & Clark LLP

(57) ABSTRACT

Washing with conventional filmy soaps cannot bring about clean detergent effect because of the remaining sliminess due to the ingredient essential for forming soap into films. Further, when moisture adheres to conventional filmy compositions, the water-soluble polymer or other ingredients contained in the compositions dissolve in the moisture to cause the blocking of filmy compositions, which makes it impossible to take out the filmy compositions one by one. Detergent effect without sliminess and the antiblocking of filmy compositions can be attained by incorporating a granular component into a filmy composition containing a water-soluble polymer. The filmy compositions of the invention are used as filmy facial masks, whitening masks, sheet soap, cleansing sheets, sheet shampoos, sheet rinses, sheet bath additives, and so on.

14 Claims, No Drawings

FILMY COMPOSITIONS

TECHNICAL FIELD

The present invention relates to a film-like composition which is suitable for applications such as facial masks, whitening masks, sheet soap, face washing sheets, sheet shampoo, sheet rinses, and sheet bath agents in the form of films, and which is more portable and is more reliable in allowing one sheet to be taken out at a time without the layers of the film-like composition sticking to each other when the film-like composition is stored in layers over long periods of time.

BACKGROUND ART

Film-like compositions are widely known as portable detergents, as indicated in the following Patent Citations. As described in Japanese Unexamined Patent Application (Kokai) 53-91913, for example, known film-like compositions comprise an aliphatic soap and a water-soluble polymer such as methyl cellulose or polyvinyl alcohol. A disadvantage of using the above film-like compositions, however, is that a slimy feel is left over by the action of the methyl cellulose or polyvinyl alcohol which are key ingredients for forming the soap into a film, thereby preventing the desired clean, refreshing effects from being obtained. Another major problem is that, when layered film-like compositions are placed in cases or pouches to be used one layer at a time, the adhesion of moisture to the film-like composition may result in the release of the water-soluble polymer or contents, and the layers of the film-like composition may become stuck together, making it impossible to take out one sheet at a time. This may happen when moisture in the air is absorbed or moisture on the hands is transferred to the film-like composition as the film-like composition is taken out, thus leading to a loss of usability over the long term. The present invention is intended to overcome such drawbacks. An object is to prevent the layers of film-like compositions from adhering to each other and to improve the usability of film-like compositions.

Patent Citation 1: Laid-open Japanese Patent (Kokai) No. S53-91912
Patent Citation 2: Laid-open Japanese Patent (Kokai) No. S53-91913
Patent Citation 3: Laid-open Japanese Patent (Kokai) No. S62-81432
Patent Citation 4: Laid-open Japanese Patent (Kokai) No. H2-22400
Patent Citation 5: Laid-open Japanese Patent (Kokai) No. 2003-147400

DISCLOSURE OF THE INVENTION

The present invention is intended to overcome the above drawbacks, and is intended to provide a film-like composition which can be used by being taken out one layer at a time without the layers of the film-like composition sticking to each other even when moisture adheres to the film-like composition during use or storage. The present invention may also be in the form of a film-like composition comprising a surfactant ingredient, in which the effect of the granule ingredients included in the film-like composition result in better scrubbing effects during cleansing, without leaving a slimy feel. The scrubbing effects signify the effects of removing stratum corneum that persisted for some time.

A film-like composition which contains at least a water-soluble polymer compound and forms a sheet when dried, is characterized by comprising granule ingredients.

The film-like composition is also characterized in that granule ingredients are granulated granules.

The film-like composition is also characterized in that the mean particle diameter of the granule ingredients is 5 to 400 μm, and preferably 20 to 200 μm.

The film-like composition is also characterized in that the granule ingredients are included in an amount of 0.1 to 20 mass %, and preferably 1 to 15 mass %, relative to the film-like composition as a whole after drying.

The film-like composition is also characterized by comprising a surfactant ingredient, thereby having detergent properties.

The film-like composition is also characterized by comprising a moisturizing ingredient, thereby having moisturizing properties.

In the present invention, granule ingredients are blended with the film-like composition to prevent the layers of the film-like composition from becoming stuck to each other, even if moisture adheres to the film-like composition, when placed in layers in a case. The layers can also be sure to be taken out one at a time up to the last layer over long periods of time. As the film-like composition is generally commercially available in portable form, being able to ensure that the layers can be taken out one at a time up to the last layer will significantly enhance the commercial value in particular. Furthermore, when granule ingredients and surfactant ingredients are included in the film-like composition, the granule ingredients will result in better scrubbing effects during cleansing, without leaving a slimy feel.

BEST MODE FOR CARRYING OUT THE INVENTION

The invention is described in greater detail below. The water-soluble polymer compound used in the invention may be any that is water-soluble and that forms a coating in the form of a film after drying. Examples include celluloses such as cellulose and cellulose ethers (such as methyl cellulose, hydroxyethylmethyl cellulose, hydroxypropylmethyl cellulose, hydroxybutylmethyl cellulose, hydroxyethyl cellulose, hydroxypropyl cellulose, hydroxybutyl cellulose, and carboxymethyl cellulose); polyvinyl alcohols; starches; polysaccharides such as pullulan and sodium hyaluronate; water-soluble collagen; sodium alginate; and polyvinyl pyrrolidone. Hydroxypropylmethyl cellulose, hydroxypropyl cellulose, starches, or pullulan are particularly desirable. The above water-soluble polymer compounds may be used alone or in combinations of two or more.

The content of the undried water-soluble polymer compound in the film-like composition should be 2 to 50 mass %, preferably 4 to 20 mass % in the case of hydroxypropylmethyl cellulose and hydroxypropyl cellulose in particular, and 10 to 45 mass % in the case of starches and pullulan. If the content of the water-soluble polymer compound is too low, the composition cannot be formed into a film, whereas if the content is too great, the water-soluble polymer compound will become pasty when used, resulting in poor usability. The content in the dried film-like composition should be 15 to 45 mass %.

Granulated granules can be used as the granule ingredients in the present invention. The mean particle diameter of the granule ingredients includes a variety of grades, ranging from fine particles on the order of several μm to those with a mean particle diameter in the hundreds of μm which provide a scrubbing impression, but any granulated granules used in common cosmetics can be used as the granule ingredients in the present invention. To prevent the layers of the dried film-like composition from sticking together, the mean particle diameter of the granule ingredients should be 5 to about 400 μm, and preferably 20 to 200 μm.

The content of the granule ingredients in the dried film-like composition should be 0.1 to 20 mass %, and preferably 1 to 15 mass %. Less than 0.1 mass % will make it difficult to bring about the adhesion-preventing function, while more than 20 mass % will result in a pronounced feeling of roughness when used, giving a poor impression of use.

The granule ingredients can be colored with a dye, medical agent, or the like. It is well known that they can be colored and dispersed in the film-like composition to further enhance the aesthetic appeal of the film-like composition while preserving the scrubbing effects.

The granulated granules serving as the granule ingredients may be common granulated granules comprising powder ingredients fused together into the form of granules. Methods of production include wet drying, extrusion granulation, and fluidized bed granulation, where granulation is brought about when water, solvent, or the like in which a binder has been dissolved is sprayed as uniformly mixed powder is suspended in a fluid layer.

Examples of powder used for the granulated granules in the present invention include common inorganic pigments such as zinc oxide, talc, mica, sericite, titanium oxide, iron oxide, kaolin, or silica, or water-insoluble salts such as calcium carbonate or calcium phosphate. General purpose polymer materials can also be used. Examples include hydrocarbon polymers such as polyethylene, polypropylene, and polystyrene, polyamide methacrylate polymers such as nylon, as well as polyurethane polymers, silicon polymers, and copolymers thereof. The water-soluble powder can be combined with the above ingredients. Dyes, chemicals, and the like can also be blended as needed in the powder.

These powders may be granulated, alone or in combinations of two or more, in the usual manner using a binder to produce the granulated granules employed in the invention.

Besides oil-based binders, examples of binders which can be used include hydrophilic cellulose polymers such as hydroxyethyl cellulose and hydroxymethyl cellulose, and hydrophobic cellulose polymers such as ethyl cellulose and methyl cellulose, as well as polyethylene glycol.

Examples of solvents which may be used to dissolve the binder include any solvents which are not very irritating on the skin, such as ethanol and acetone.

Surfactant ingredients may be used, particularly when the film-like composition is made in the form of sheet soap, sheet shampoo, or a sheet rinse. Examples of surfactants which can be used include anionic surfactants such as fatty acid alkali salts, N-long chain acylamino acid salts, alkyl sulfate esters, and polyoxyethylene alkyl ether sulfates; amphoteric surfactants such as imidazoline and betaine amphoteric surfactants; nonionic surfactants such as polyoxyethylene alkyl ethers, polyoxyethylene fatty acid esters, sucrose fatty acid esters, alkyl glycosides, and maltitol hydroxy fatty acid esters; and cationic surfactants such as trimethyl alkyl ammonium chloride.

Examples of fatty acids for fatty acid alkali salts include $C_8$ to $C_{24}$, and preferably $C_{12}$ to $C_{18}$ linear or branched, saturated or unsaturated fatty acids. Specific examples of desirable fatty acids include saturated fatty acids such as lauric acid, myristic acid, palmitic acid, stearic acid, and isostearic acid, unsaturated fatty acids such as oleic acid, and mixtures of these such as coconut oil fatty acids, palm oil fatty acids, palm kernel oil fatty acids, tallow fatty acids, and hydrogenated tallow fatty acids.

Examples of alkalis for the above fatty acid alkali salts include alkali metals such as sodium, potassium, and lithium, alkaline earth metals such as calcium and magnesium, and organic amines such as (mono-, di-, tri-) ethanolamines and basic amino acids (such as lysine, arginine, and histidine). Specific examples of desirable alkalis include sodium and potassium. Fatty acid alkali salts can be used alone or in combinations of two or more.

The content of the fatty acid alkali salt in the dried film-like composition is preferably 15 to 65 mass %, and more preferably 20 to 60 mass %. A content that is too low will result in poor hardening, while a content that is too great will result in a film-like composition that is hard or brittle and lacking in plasticity.

Other additives that may be added as needed to the film-like composition of the present invention include moisturizers such as glycerol, diglycerol, 1,3-butylene glycol, propylene glycol, dipropylene glycol, polyethylene glycol, sucrose, sorbitol, and sodium hyaluronate, chelators such as edetates, plant extracts such as *Swertia japonica, Paeonia albiflora, Iris, Equisetum arvense, aloe*, chamomile, *Eucalyptus* oil, and dipotassium glycyrrhizinate, medicinal agents such as tranexamic acid and arbutin, fragrances, dyes, and antiseptics.

Compounds represented by the following General Formula (A) can also be added to the film-like composition of the invention to enhance transparency and detergency.

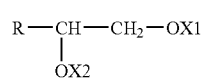

General Formula (A)

(where R is a $C_4$ to $C_{34}$ alkyl or $C_4$ to $C_{34}$ alkenyl, at least one of X1 and X2 is —$CH_2COOM$ and the other is a hydrogen atom, and M is an alkali metal, alkaline earth metal, ammonium, lower alkanolamine cation, lower alkylamine cation, or basic amino acid cation).

The compounds of General Formula (A) have been disclosed in Laid-open Japanese Patent (Kokai) No. S63-280798, where the $C_4$ to $C_{34}$ alkyl represented by R includes linear or branched alkyls such as butyl, hexyl, octyl, decyl, dodecyl, tetradecyl, hexadecyl, octadecyl, eicosyl, docosyl, tetracosyl, 2-ethylhexyl, 2-hexyldecyl, 2-octylundecyl, 2-decyltetradecyl, and 2-undecylhexadecyl. The $C_4$ to $C_{34}$ alkenyl is a linear or branched alkenyl such as octenyl, decenyl, dodecenyl, tetradecenyl, hexadecenyl, and octadecenyl. R in General Formula (A) is preferably a $C_8$ to $C_{18}$ linear alkyl, especially decyl or dodecyl, as the film-like composition will have particularly good lathering properties.

Examples of alkali metals for M in General Formula (A) include sodium, potassium, and lithium. Examples of alkaline earth metals include calcium, magnesium, and barium. Examples of lower alkanolamines for forming lower alkanolamine cation include $C_1$ to $C_4$ alkanolamines such as ethanolamine, n-propanolamine, and isopropanolamine, which may be in the mono-, di-, or tri-form of the compounds. Examples of lower alkylamines for forming lower alkylamine cations include $C_1$ to $C_4$ alkylamines such as methylamine, ethylamine, n-propylamine, and isopropylamine, which may be in the mono-, di-, or tri-form of the compounds. Examples of basic amino acids for forming basic amino acid cations include lysine, arginine, ornithine, and histidine. M in General Formula (A) is preferably an alkali metal or lower alkanolamine cation, especially sodium or potassium, as the film-like composition will have particularly good lathering properties.

In General Formula (A), at least one of X1 and X2 is —CH$_2$COOM, and the other is a hydrogen atom. Blending a compound (c) having such a structure will enhance the solubility and lathering properties of the transparent film-like composition. Specific examples of compound (c) include sodium octane-1,2-diol acetate ether, sodium decane-1,2-diol acetate ether, sodium dodecane-1,2-diol acetate ether, sodium tetradecane-1,2-diol acetate ether, sodium hexadecane-1,2-diol acetate ether, and sodium octadecane-1,2-diol acetate ether. Compound (c) may be one in which either X1 or X2 is —CH$_2$COOM, both X1 and X2 are —CH$_2$COOM, or mixtures thereof. The above compounds (c) may be used alone or in combinations of two or more.

Compound (c) can be obtained, where M is sodium, for example, by converting an alkyl-1,2-diol to an alcoholate using metallic sodium or the like in an ether solvent such as dioxane in a nitrogen current, and then bringing about a reaction with sodium chloroacetate. The content of the above compound (c) in the transparent film-like composition is preferably 2 to 25 mass %, and more preferably 3 to 15 mass %. A content that is too low will not provide adequate solubility or lathering properties, resulting in a film-like composition of no practical use, whereas a content that is too high will result in considerable stickiness and thus the risk of poor film formability.

A moisturizer may be blended in facial masks and whitening facial masks in the form of a film in the present invention. Examples of moisturizers include those blended in common cosmetic materials, such as polyethylene glycol, propylene glycol, glycerol, 1,3-butylene glycol, xylitol, sorbitol, maltitol, chondroitin sulfate, hyaluronic acid, mucoitin sulfate, charonin sulfuric acid, atelocollagen, cholesteryl 12-hydroxystearate, sodium lactate, bile salts, dl-pyrrolidonecarboxylates, short chain soluble collagen, diglycerol (EO) PO adducts, *rosa roxburghii* fruit extract, *achillea millefolium* extract, and melilot extract.

The amount in which such moisturizers are blended will vary depending on the intended film-like composition, but is 3 to 20 mass % in whitening facial masks and cosmetic sheets in the form of dry films. The moisturizer can be blended in the form of a solution during the manufacture of the film-like composition, but it can also be introduced in advance into the granulated granules, which may then be added during the manufacturing process.

A variety of medicinal agents can also be blended into whitening facial masks and cosmetic sheets in the form of films. Examples include whitening agents such as L-ascorbic acid and derivatives thereof, glutathione, tranexamic acid and derivatives thereof, arbutin, alkoxysalicylic acid and derivatives thereof, kojic acid and derivatives thereof, ellagic acid, resorcin derivatives, and chamomile extract.

These medicinal agents can be blended in the form of a solution during the manufacture of the film-like composition, but if there are any problems in terms of stability, they can also be blended into the granulated granules. The medicinal agents are blended in the same amounts used in common cosmetics.

The film-like composition of the invention can be prepared in the form of a film by conventionally known methods after the composition has been mixed and dissolved to homogeneity to prepare a stock solution. The film may be produced, for example, by supplying the stock solution prepared above onto a substrate surface heated to between about 60 and 90° C., where it is cast and dried. The solution should be cast so as to result in a dry thickness of 20 to 180 μm.

The compound (c) of General Formula (A) above may also be blended into the composition in order to lower the Kraft point and thus enhance the solubility, while the superior lathering properties inherent to compound (c) will also enhance the lathering properties of the composition. This will allow a thin, transparent film to be formed, and will also provide a film-like composition of better design potential, portability, and usability, and which will dissolve rapidly, affording good lathering properties and scrubbing effects, without causing the layers of the film-like composition to become stuck together.

The adhesion and film formability of the film-like composition of the invention were assessed using the following test methods. Film-like compositions which had been produced were cut to a size of 6 cm×6 cm, 60 layers of the cut film-like composition were stacked, and the stacks were stored for 4 weeks in a thermostatic tank at 40° C. and 70% humidity. The layers were taken out of the thermostatic tank after 4 weeks, and three judges determined whether the layers could be separated one layer at a time according to the following criteria.

⊚: Each layer could be separated without any sticking whatsoever.

The surface was not sticky at all.

◯: Each layer could be separated without any sticking.

The surface was somewhat sticky.

Δ: 10 or less out of 60 layers became stuck. The surface was also sticky.

X: 11 or more out of 60 layers became stuck. The surface was very sticky.

EXAMPLE 1

Based on the following formulation, a face washing sheet in the form of a film was prepared, in which granulated granules with a mean particle diameter of 100 μm had been blended as the granule ingredients.

|  | Face Washing Sheet (mass %) |
|---|---|
| 1. hydroxypropyl cellulose | 18.8 |
| 2. sodium laurate | 37.8 |
| 3. coconut oil fatty acid amidopropyl betaine | 11.0 |
| 4. glycerol | 13.4 |
| 5. granulated granules*1 | 9.0 |
| 6. deionized water | 10.0 |

Preparation 20 mass % aqueous solution of hydroxypropyl cellulose was prepared, 30 mass % aqueous solution of coconut oil fatty acid amidopropyl betaine was prepared, ingredients 1 to 6 were dissolved at 60° C. to give a homogenous solution, and the solution was cast on glass plates using a 500 μm casting tool (doctor blade) and was dried in a thermostatic tank to a moisture content of 10%, giving a 130 μm thick film. The film was cut to a size of 6 cm×6 cm, giving a face washing sheet in the form of a film. The adhesion of the face washing sheet was checked by the test method described above. The layers could be separated one at a time, without any sticking, resulting in a rating of ⊚.

*1 The granulated granules used here had the following composition.

|   | (mass %) |
|---|---|
| 1. powdered polyethylene | 79.0 |
| 2. talc | 10.0 |
| 3. ethyl cellulose (binder) | 5.0 |
| 4. yellow iron oxide | 5.0 |
| 5. powdered aloe | 1.0 |

Preparation

Ingredients 1 to 5 were mixed and milled to homogeneity using a Henschel mixer, and ethanol was kneaded in. The mixture was then extruded through a 20 mesh screen using an oscillator and granulated, and the granules were dried for 2 days at room temperature, allowing the ethanol to evaporate off. The particle size of the granules was then adjusted by being again extruded through a 24 mesh screen, and they were furthermore sifted to a mean particle size of 100 μm using a shaking sieve, giving granulated granules.

EXAMPLE 2

Based on the following formulation, a sheet shampoo in the form of a film was prepared, in which granulated granules with a mean particle diameter of 150 μm had been blended as the granule ingredients.

|   | Sheet shampoo (mass %) |
|---|---|
| 1. pullulan | 44.0 |
| 2. sodium laurate | 10.0 |
| 3. coconut oil fatty acid amidopropyl betaine | 17.6 |
| 4. diglycerol | 8.8 |
| 5. granulated granules*2 | 7.6 |
| 6. deionized water | 12.0 |

Preparation 20 mass % aqueous solution of pullulan was prepared, 30 mass % aqueous solution of coconut oil fatty acid amidopropyl betaine was prepared, ingredients 1 to 6 were dissolved at 60° C. to give a homogenous solution, and the solution was cast on glass plates using a 500 μm casting tool (doctor blade) and was dried in a thermostatic tank to a moisture content of 10%, giving a 130 μm thick film. The film was cut to a size of 6 cm×6 cm, giving a sheet shampoo in the form of a film. The adhesion of the sheet shampoo was checked by the test method described above. The layers could be separated one at a time, without any sticking, resulting in a rating of ⊚.

*2 The same granulated granules as in Example 1 were used.

EXAMPLE 3

Based on the following formulation, a whitening facial mask in the form of a film was prepared, in which granulated granules with a mean particle diameter of 200 μm had been blended as the granule ingredients.

|   | Whitening facial mask (mass %) |
|---|---|
| 1. starch | 45.0 |
| 2. pullulan | 30.0 |
| 3. sodium hyaluronate | 1.5 |
| 4. glycerol | 12.0 |
| 5. granulated granules*3 | 1.5 |
| 6. deionized water | 10.0 |

Preparation 20 mass % aqueous solution of starch and pullulan was prepared, ingredients 1 to 6 were dissolved at 60° C. to give a homogenous solution, and the solution was cast on glass plates using a 500 μm casting tool (doctor blade) and was dried in a thermostatic tank to a moisture content of 10%, giving a 200 μm thick film. The film was cut to a size of 6 cm×6 cm, giving a whitening facial mask in the form of a film. The adhesion of the whitening facial mask was checked by the test method described above. The layers could be separated one at a time, without sticking, resulting in a rating of ◯.

*3 The granulated granules used here had the following composition.

|   | (mass %) |
|---|---|
| 1. powdered polyethylene | 70.0 |
| 2. crystalline cellulose | 5.0 |
| 3. ceramide (moisturizer) | 10.0 |
| 4. ethyl cellulose (binder) | 10.0 |
| 5. arbutin | 5.0 |

Preparation

Ingredients 1 to 5 were mixed and milled to homogeneity using a Henschel mixer, and ethanol was kneaded in. The mixture was then extruded through a 20 mesh screen using an oscillator and granulated, and the granules were dried for 2 days at room temperature, allowing the ethanol to evaporate off. The particle size of the granules was then adjusted by again being extruded through a 30 mesh screen, and they were furthermore sifted to a mean particle size of 200 μm using a shaking sieve, giving granulated granules.

EXAMPLE 4

|   | Moisturizing facial mask (mass %) |
|---|---|
| 1. starch | 35.0 |
| 2. pullulan | 20.0 |
| 3. water-soluble collagen | 5.0 |
| 4. retinol | 1.0 |
| 5. silicone oil | 5.0 |
| 6. polyether-modified silicone | 5.0 |
| 7. glycerol | 15.0 |
| 8. granulated granules*4 | 5.0 |
| 9. deionized water | 9.0 |

Preparation 20 mass % aqueous solution of starch and pullulan was prepared, ingredients 1 to 6 and 8 were dissolved at 70° C. and emulsified using a homomixer, ingredient 7 was added, and the solution was cast on glass plates using a 500 μm casting tool (doctor blade) and was dried in a thermostatic tank to a moisture content of 10%, giving a 100 μm thick film. The film was cut to a size of 2 cm×2 cm, giving a moisturizing facial mask in the form of a film. The adhesion of the moisturizing facial mask was checked by the test method described above. The layers could be separated one at a time, without sticking, resulting in a rating of ○.

*4 The granulated granules used here had the following composition.

|  | (mass %) |
|---|---|
| 1. powdered polyethylene | 80.0 |
| 2. talc | 10.0 |
| 3. hydroxyproline | 5.0 |
| 4. ethyl cellulose (binder) | 3.0 |
| 5. Red Dye No. 226 | 2.0 |

Preparation

The granulated granules were obtained in the manner described above.

Face washing sheets in the form of a film comprising the composition of Example 1 were used to prepare face washing sheets in which granulated granules had been blended within the range of 0.1 to 11.2 mass %. The face washing sheets were evaluated for adhesion, foreign body sensation on the skin, film formability, and lathering. The results are given in the form of Examples 5 to 10 in Table 1 below.

TABLE 1

|  |  | Examples | | | | | | Comp. |
|---|---|---|---|---|---|---|---|---|
|  |  | 5 | 6 | 7 | 8 | 9 | 10 | Ex. 1 |
| Granule ingredients | mean particle diameter of 100 μm | 0.1 (mass %) | 0.5 (mass %) | 1 (mass %) | 5 (mass %) | 8 (mass %) | 15.0 (mass %) | — |
| Evaluation parameters | Adhesion | Δ | ○ | ◎ | ◎ | ◎ | ◎ | X |
|  | Foreign body sensation on skin | ◎ | ◎ | ◎ | ◎ | ○ | ○ | ○ |
|  | Film formability | ○ | ○ | ○ | ○ | ○ | Δ | ○ |
|  | Lathering | ○ | ○ | ○ | ○ | ○ | ○ | ○ |

The face washing sheets in the form of a film in Examples 5 to 10, which had a blend of granulated granules in the range of 0.1 to 11.2 mass %, were superior in terms of adhesion properties, foreign body sensation on the skin, film formability, and lathering. In Comparative Example 1, on the other hand, which contained no granulated granules, the layers of film became stuck to each other, precluding long term use.

Face washing sheets in the form of a film comprising the composition of Example 1 were used to prepare face washing sheets in which 5 mass % granulated granules had been blended and the mean particle diameter of the granules had been sorted within the range of 5 to 400 μM. The face washing sheets were evaluated for adhesion, foreign body sensation on the skin, film formability, and lathering. The results are given in the form of Examples 11 to 16 in Table 2 below.

TABLE 2

|  |  | Example | | | | | | Comp. |
|---|---|---|---|---|---|---|---|---|
|  |  | 11 | 12 | 13 | 14 | 15 | 16 | Ex. 2 |
| Mean particle size | 1 μm |  |  |  |  |  |  | 5 (mass %) |
|  | 5 μm | 5 (mass %) |  |  |  |  |  |  |
|  | 10 μm |  | 5 (mass %) |  |  |  |  |  |
|  | 20 μm |  |  | 5 (mass %) |  |  |  |  |
|  | 200 μm |  |  |  | 5 (mass %) |  |  |  |
|  | 300 μm |  |  |  |  | 5 (mass %) |  |  |
|  | 400 μm |  |  |  |  |  | 5 (mass %) |  |

TABLE 2-continued

|  |  | Example | | | | | | Comp. |
|---|---|---|---|---|---|---|---|---|
|  |  | 11 | 12 | 13 | 14 | 15 | 16 | Ex. 2 |
| Evaluation parameters | Adhesion | Δ | ○ | ◎ | ◎ | ◎ | ◎ | X |
|  | Foreign body sensation on skin | ◎ | ◎ | ○ | ○ | ○ | Δ | ◎ |
|  | Film formability | ○ | ○ | ○ | ○ | ○ | Δ | ○ |
|  | Lathering | ○ | ○ | ○ | ○ | ○ | Δ | ○ |

The face washing sheets in the form of a film in Examples 11 to 16, which contained 5 mass % granulated granules, and for which the mean particle diameter of the granules was sorted within the range of 5 to 400 µm, were superior in terms of adhesion properties, foreign body sensation on the skin, film formability, and lathering. In Comparative Example 2, on the other hand, where the mean particle size was 1 µm, the layers of film became stuck to each other, precluding long term use.

What is claimed is:

1. A stack of a plurality of sheets, wherein each of the plurality of sheets in the stack comprises a dried film-like composition including a water-soluble polymer compound and dispersed granule ingredients, wherein said granule ingredients have a mean particle diameter of 5 µm to 400 µm and are present in the dried film-like composition in an amount of 0.1 mass % to 20 mass %, wherein the granule ingredients are granulated granules that comprise powder ingredients fused together in the form of granules, wherein the granulated granules comprise a whitening agent selected from the group consisting of ascorbic acid, glutathione, tranexamic acid, arbutin, alkoxysalicylic acid, kojic acid, ellagic acid, resorcinol and chamomile extract, wherein the granule ingredients dispersed in the dried film-like composition prevent the plurality of sheets in the stack from sticking to one another, and wherein each of the plurality of sheets in the stack is dissolvable in water.

2. The stack of the plurality of sheets of claim 1, wherein the mean particle diameter of the granule ingredients is 20 µm to 200 µm.

3. The stack of the plurality of sheets of claim 1, wherein the granule ingredients are present in the dried film-like composition in an amount of 1 mass % to 15 mass %.

4. The stack of the plurality of sheets of claim 1, wherein each of the plurality of sheets in the stack further comprises a surfactant ingredient.

5. The stack of the plurality of sheets of claim 1, wherein the granule ingredients further comprise inorganic pigments, water-insoluble salts, polymer materials, or combinations thereof.

6. The stack of the plurality of sheets of claim 1, wherein the granule ingredients further comprise zinc oxide, talc, mica, sericite, titanium oxide, iron oxide, kaolin, silica, calcium carbonate, calcium phosphate, polyethylene, polypropylene, polystyrene, nylon, polyurethane polymers, silicon polymers, or combinations thereof.

7. The stack of the plurality of sheets of claim 1, wherein the granule ingredients further comprise talc and polyethylene.

8. The stack of the plurality of sheets of claim 1, wherein each of the plurality of sheets in the stack further comprises glycerol, diglycerol, 1,3-butylene glycol, propylene glycol, dipropylene glycol, polyethylene glycol, sucrose, sorbitol, sodium hyaluronate, chelators, plant extracts of *Swertia japonica, Paeonia albiflora, Iris, Equisetum arvense*, aloe, and *Eucalyptus* oil, dipotassium glycyrrhizinate, or combinations thereof.

9. The stack of the plurality of sheets of claim 1, wherein the granule ingredients prevent the sheets from sticking to one another after the stack of the plurality of sheets has been stored for 4 weeks in a thermostatic tank at 40° C. and 70% humidity.

10. The stack of the plurality of sheets of claim 1, wherein each of the plurality of sheets is obtained by heating a solution comprising the water-soluble polymer compound and the granule ingredients at 60° C. to 90° C. and casting the heated solution on a substrate.

11. The stack of the plurality of sheets of claim 1, wherein the granule ingredients have a mean particle diameter of 100 µm to 400 µm and are present in the dried film-like composition in an amount of 1 mass % to 15 mass %.

12. A stack of a plurality of sheets, wherein each of the plurality of sheets in the stack comprises a dried film-like composition including:

a water-soluble polymer; and granulated granules comprising powder ingredients fused together into the form of granules using a binder;

wherein the granulated granules have a mean particle diameter of 5 µm to 400 µm and are incorporated into the dried film-like composition an amount of 0.1 mass % to 20 mass %, wherein the granule ingredients are granulated granules that comprise powder ingredients fused together in the form of granules, wherein the granulated granules comprise polyethylene, talc, ethylene cellulose as a binder, a moisturizer and a whitening agent, wherein the granulated granules prevent the plurality of sheets in the stack from sticking to one another, wherein the dried film-like composition further optionally comprises chelators, plant extracts, medical agents, fragrances, dyes, or antiseptics, and wherein each of the plurality of sheets in the stack is a facial mask, whitening mask, sheet soap, face washing sheet, sheet shampoo, sheet rinse, or sheet bath agent.

13. The stack of the plurality of sheets of claim 12, wherein the moisturizer comprises powdered aloe.

14. The stack of the plurality of sheets according to claim 12, wherein the moisturizer comprises ceramide and the whitening agent comprises arbutin.

* * * * *